United States Patent [19]

Ueda et al.

[11] 4,370,340
[45] Jan. 25, 1983

[54] BENZOTHIAZOL-2-ONE-3-ALKANOIC ACIDS AND ESTERS AND ALDOSE REDUCTASE INHIBITING COMPOSITIONS THEREOF

[75] Inventors: Ikuo Ueda; Masaaki Matsuo, both of Toyonaka; Susumu Satoh, Ikeda; Takao Watanabe, Mukou, all of Japan

[73] Assignee: Fujisawa Pharmaceutical Co., Ltd., Osaka, Japan

[21] Appl. No.: 155,185

[22] Filed: Jun. 2, 1980

[30] Foreign Application Priority Data

Jun. 12, 1979 [JP] Japan ................................. 54-74239

[51] Int. Cl.³ ................ C07D 277/68; A61K 31/425
[52] U.S. Cl. ..................................... 424/274; 548/170
[58] Field of Search .......................... 548/170; 424/274

[56] References Cited

U.S. PATENT DOCUMENTS 4,049,419  9/1977  D'Amico ............................. 71/76

FOREIGN PATENT DOCUMENTS 2037999  2/1971  Fed. Rep. of Germany ...... 548/170

*Primary Examiner*—Donald G. Daus
*Assistant Examiner*—D. B. Springer
*Attorney, Agent, or Firm*—Oblon, Fisher, Spivak, McClelland & Maier

[57] ABSTRACT

A pharmaceutical composition comprising certain benzothiazoline alkanoic acid derivatives for the prevention and treatment of various diabetic complications, said derivatives being inhibitors of aldose reductase.

4 Claims, No Drawings

BENZOTHIAZOL-2-ONE-3-ALKANOIC ACIDS AND ESTERS AND ALDOSE REDUCTASE INHIBITING COMPOSITIONS THEREOF

This invention relates to a new pharmaceutical composition comprising certain lower alkanoic acid derivatives. More particularly, it relates to a new pharmaceutical composition for the prevention and treatment of various diabetic complications comprising the lower alkanoic acid derivatives as an active ingredient, and to new compounds among the lower alkanoic acid derivatives and to processes for their preparation.

This invention based on the discovery by the present inventors that certain lower alkanoic acid derivatives are highly potent inhibitors of aldose reductase and therefore useful for the prevention and treatment of various diabetic complications (e.g. cataracts, neuropathy, retinopathy and nephropathy).

In this respect, it has been already known that spiro-hydantoin compounds and 5,6-dihydro-4H-pyrrolo-[3,2,1-ij]quinolin-1,2-dione are aldose reductase inhibitors [cf. U.S. Pat. Nos. 4,117,230 (1978) and 4,151,282 (1979)]. However, the aldose reductase inhibitors of this invention are structurally different from those prior compounds.

Accordingly, one object of this invention is to provide a pharmaceutical composition for preventing and treating diabetic complications comprising, as an active ingredient, at least one of the lower alkanoic acid derivatives.

Another object of this invention is to provide new lower alkanoic acid derivatives.

Further object of this invention is to provide processes for the preparation of new lower alkanoic acid derivatives.

The lower alkanoic acid derivatives can be represented by the formula:

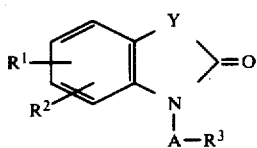

(I)

wherein
  $R^1$ is hydrogen, hydroxy, nitro, amino, lower alkoxy, halogen, ($C_3$ to $C_8$)cycloalkyl, aryl or aryloxy which may be substituted with halogen,
  $R^2$ is hydrogen, halogen or lower alkyl,
  $R^3$ is carboxy or a protected carboxy group,
  Y is sulfur, oxygen, carbonyl or methylene and
  A is lower alkylene,
and pharmaceutically acceptable salts thereof.

Among the compounds represented by the above formula (I), preferred new compounds of this invention can be represented by the formula:

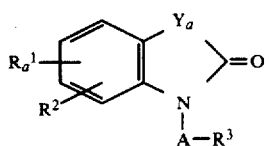

(Ia)

wherein $R_a{}^1$ is hydroxy, halogen, nitro, amino, ($C_3$ to $C_8$)cycloalkyl, aryl or aryloxy which may be substituted with halogen, $Y_a$ is sulfur, oxygen or methylene, $R^2$, A and $R^3$ are each as defined above, provided that when $R^2$ is hydrogen and $Y_a$ is sulfur or oxygen, $R_a{}^1$ is not halogen, and pharmaceutically acceptable salts thereof.

The new object compound (Ia) can be prepared by the following Precesses.

Process 1

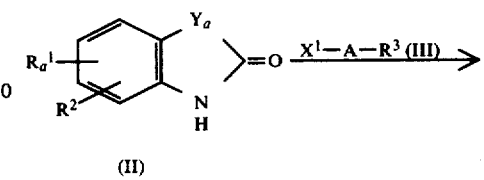

(II)

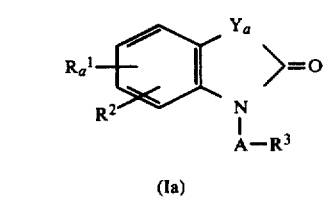

(Ia)

Process 2

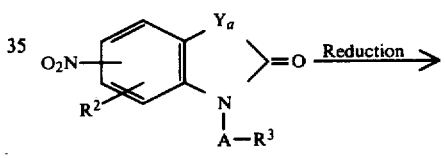

($I_a{}^1$)

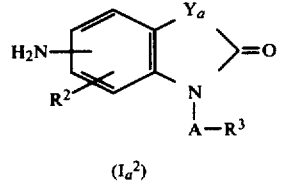

($I_a{}^2$)

Process 3

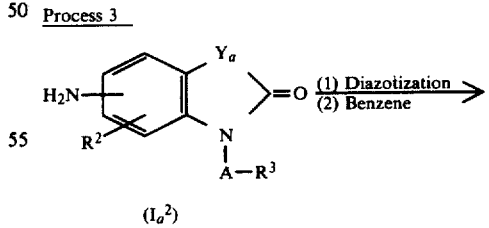

($I_a{}^2$)

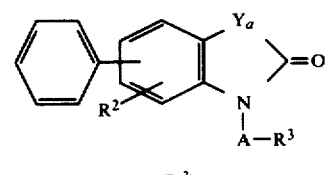

($I_a{}^3$)

Process 4

-continued

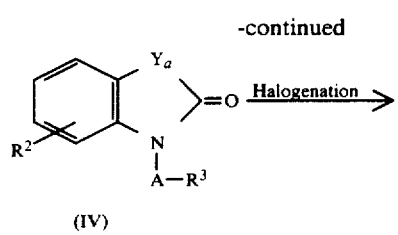

(IV)

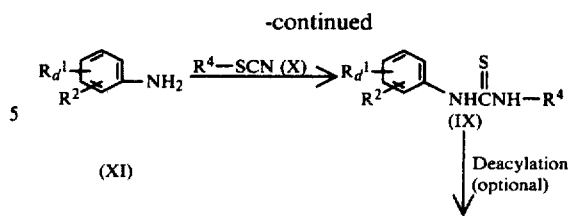

(XI) (IX)

↓ Deacylation (optional)

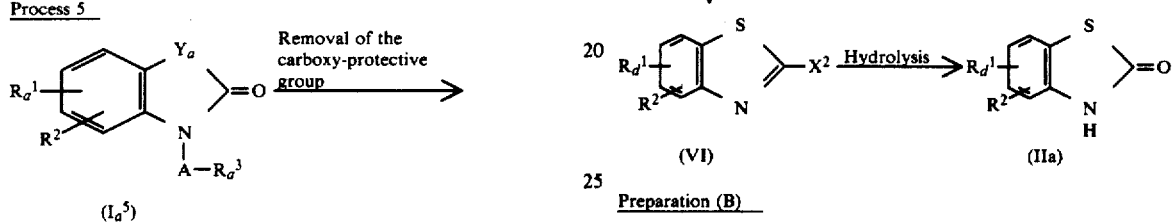

(VII) (VIII)

↓ (1) Diazotization
(2) Cupric halide (VI) →Hydrolysis→ (IIa)

Preparation (B)

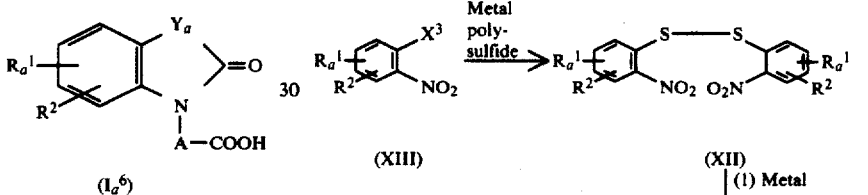

(XIII) (XII)

↓ (1) Metal monosulfide
(2) COCl₂

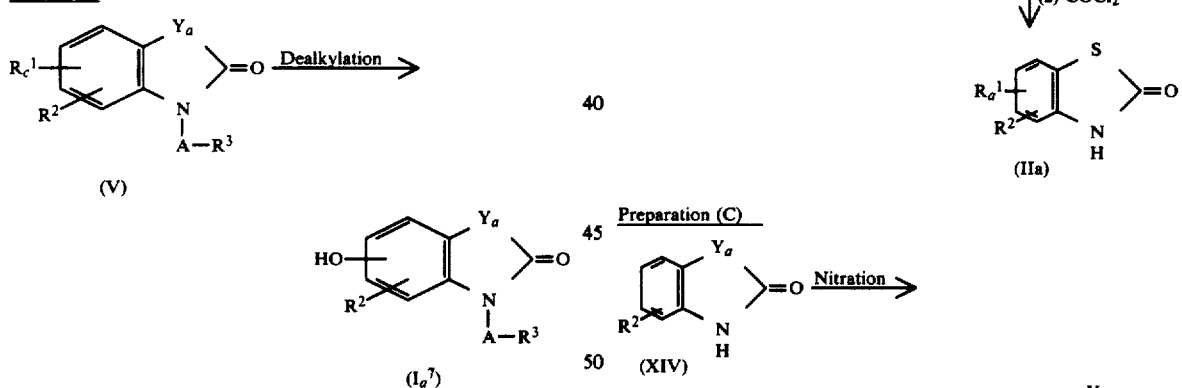

Process 5

(I$_a^5$) →Removal of the carboxy-protective group→

(I$_a^6$)

Process 6

(V) →Dealkylation→

(IIa)

Preparation (C)

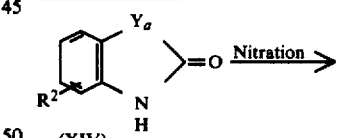

(XIV) →Nitration→

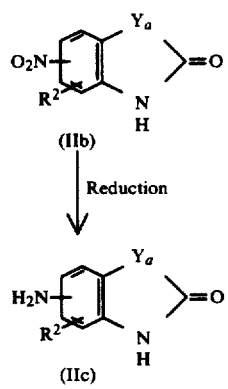

(IIb)

↓ Reduction (IIc)

wherein
R$_a^1$, R², R³, Y$_a$ and A are each as defined above,
R$_b^1$ is halogen,
R$_c^1$ is lower alkoxy,
R$_a^3$ is a protected carboxy and
X¹ is an acid residue.

Among the starting compound (II), novel compound can be prepared by the following Preparations (A), (B) and (C) and the others can be prepared by the similar manner thereto.

Preparation (A)

wherein
R$_a^1$, R² and Y$_a$ are each as defined above, $R_d^1$ is hydroxy, halogen, nitro, ($C_3$ to $C_8$)cycloalkyl, aryl or aryloxy which may be substituted with halogen, $R^4$ is hydrogen or acyl, and $X^2$ and $X^3$ are each halogen.

In the above and subsequent description of the present specification, suitable examples for various definitions to be included within the scope of the invention are explained in details as follows.

The term "lower" means 1 to 6 carbon atom(s), unless otherwise indicated.

Suitable "lower alkoxy" may include methoxy, ethoxy, propoxy, isopropoxy, butoxy, pentyloxy, hexyloxy and the like.

Suitable "halogen" may include fluorine, chlorine, bromine or iodine.

Suitable "lower alkyl" may include methyl, ethyl, propyl, isopropyl, butyl, pentyl, hexyl and the like.

Suitable "protected carboxy group" may include an esterified carboxy group such as lower alkoxycarbonyl (e.g. methoxycarbonyl, ethoxycarbonyl, propoxycarbonyl, butoxycarbonyl, pentyloxycarbonyl, hexyloxycarbonyl, etc.) and the like.

Suitable "lower alkylene" may include methylene, ethylene, ethylidene, trimethylene, propylene, tetramethylene, pentamethylene, hexamethylene and the like.

Suitable "acid residue" may include halogen as exemplified above, azido, acyloxy (e.g. benzene-sulfonyloxy, tosyloxy, etc.) and the like.

Suitable "($C_3$ to $C_8$)cycloalkyl" may include cyclopropyl, cyclopentyl, cyclohexyl, cycloheptyl, cyclooctyl and the like.

Suitable "aryl" and "aryl moiety" in the term "aryloxy which may be substituted with halogen" may include, phenyl, tolyl, xylyl, naphthyl and the like.

Suitable "acyl" may include aliphatic acyl group and acyl group containing an aromatic or heterocyclic ring. And, suitable examples of the said acyl may be lower alkanoyl (e.g. formyl, acetyl, etc.), lower alkoxycarbonyl (e.g. methoxycarbonyl, ethoxycarbonyl, tert-butoxycarbonyl, etc.), lower alkanesulfonyl (e.g. mesyl, ethanesulfonyl, etc.), arenesulfonyl (e.g. benzensulfonyl, tosyl, etc.), aroyl (e.g. benzoyl, toluoyl, etc.), phenyl(lower)alkanoyl (e.g. phenylacetyl, phenylpropionyl, etc.), phenoxy(lower)alkanoyl (e.g. phenoxyacetyl, etc.), and the like.

The pharmaceutically acceptable salts of the compound (I) and (Ia) may include an inorganic or organic base salt such as a metal salt (e.g. sodium salt, potassium salt, magnesium salt, calcium salt, etc.), ammonium salt, an amine salt (e.g. ethanolamine salt, trimethylamine salt, triethylamine salt, dicyclohexylamine salt, etc.), an amino acid salt (e.g. arginine salt, etc.) and an inorganic or organic acid salt (e.g. hydrochloride, sulfate, etc.).

The processes for the preparation of the preferred new object compound (Ia) of this invention are explained in details as follows.

PROCESS 1

The object compound (Ia) or its salt can be prepared by reacting the compound (II) or its salt with the compound (III) or its salt.

Suitable salt of the compound (II) may include a metal salt and an acid salt as exemplified for the compound (Ia).

Suitable salt of the compound (III) may include an inorganic or organic base salt as exemplified for the compound (Ia).

This reaction is usually carried out in a conventional solvent such as acetone, chloroform, benzene, tetrahydrofuran, dimethylsulfoxide, N,N-dimethylformamide or any other solvent which does not adversely influence the reaction.

This reaction is preferably carried out in the presence of an inorganic or organic base.

The suitable base may include an inorganic or organic base such as alkali metal hydroxide (e.g. sodium hydroxide, potassium hydroxide, etc.), an alkaline earth metal hydroxide (e.g. magnesium hydroxide, calcium hydroxide, etc.), an alkali metal carbonate (e.g. sodium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), a trialkylamine (e.g. trimethylamine, triethylamine, etc.), pyridine, picoline, a diazabicyclo compound (1,5-diazabicyclo[4,3,0]nonene-5, 1,5-diazabicyclo[5,4,0]undecene-5, 1,4-diazabicyclo[2,2,2]octane, etc.), an alkali metal acetate (e.g. sodium acetate, potassium acetate, etc.), an alkali metal lower alkoxide (e.g. sodium methoxide, sodium ethoxide, potassium t-butoxide, etc.) and the like.

This reaction temperature is not critical and the reaction is usually carried out at ambient temperature or under heating.

PROCESS 2

The compound ($I_a^2$) or its salt can be prepared by reducing the compound ($I_a^1$) or its salt.

Suitable salt of the compound ($I_a^1$) may include an inorganic or organic base salt as exemplified for the compound (Ia).

This reduction is carried out by a conventional method such as a method of using a combination of metal (e.g. iron, tin, etc.) and acid (e.g. hydrochloric acid, etc.), a catalytic reduction using a conventional catalyst (e.g. Raney nickel, platinum on carbon, palladium on carbon, etc.) and the like.

This reduction is usually carried out in a conventional solvent such as water, methanol, ethanol, tetrahydrofuran, ethyl, acetate, acetic acid or any other solvent which does not adversely influence the reaction.

This reaction temperature is not critical and the reaction is usually carried out at ambient temperature or under heating.

PROCESS 3

The compound ($I_a^3$) or its salt can be prepared by reacting the compound ($I_a^2$) or its salt with a diazotizing agent and then reacting the resultant compound with benzene.

Suitable salt of the compound ($I_a^2$) may include the ones as exemplified for the compound (Ia).

Suitable examples of the diazotizing agent may include a lower alkyl nitrite (e.g. methyl nitrite, ethyl nitrite, propyl nitrite, butyl nitrite, t-butyl nitrite, etc.) an alkali metal nitrite (e.g. sodium nitrite, etc.) and the like.

This diazotization reaction is usually carried out in a solvent such as water or any other solvent which does not adversely influence the reaction.

This diazotization can be preferably carried out in the presence of a mineral acid such as hydrochloric acid, sulfuric acid, and the like.

This reaction temperature is not critical and the reaction is usually carried out under cooling or at ambient temperature.

Thus obtained reaction mixture can be used in the subsequent reaction.

The subsequent reaction using benzene is usually carried out in the presence of an inorganic or organic base such as alkali or alkaline earth metal hydroxide (e.g. sodium hydroxide, etc.), alkali metal acetate (e.g. sodium acetate, etc.) and the like.

This reaction temperature is not critical and the reaction is usually carried out under cooling or at ambient temperature.

PROCESS 4

The compound $(I_a{}^4)$ or its salt can be prepared by reacting the compound (IV) or its salt with a halogenating agent.

Suitable salt of the compound (IV) may include an inorganic and organic base salt as exemplified for the compound (Ia).

Suitable examples of the halogenating agent may include chlorine, bromine, iodine, N-chlorosuccinimide, N-bromosuccinimide, N-bromophthalimide and the like.

This reaction is usually carried out in a conventional solvent such as methanol, ethanol, chloroform, dioxane or any other solvent which does not adversely influence the reaction.

This reaction temperature is not critical and the reaction is usually carried out under cooling to warming.

PROCESS 5

The compound $(I_a{}^6)$ or its salt can be prepared by removing the carboxy-protective group of the compound $(I_a{}^5)$ or its salt.

Suitable salt of the compound $(I_a{}^5)$ may include an acid salt as exemplified for the compound (Ia).

In this elimination reaction, all conventional methods used in the elimination reaction of the protected carboxy, for example, hydrolysis, reduction, etc. can be applicable. When the protective group is an ester, it can be eliminated by hydrolysis, reduction or by using a Lewis acid which may be suitably selected in accordance with the kind of the carboxy-protective group.

The hydrolysis is preferably carried out in the presence of a base as exemplified in Process 1 or an inorganic or organic acid (e.g. hydrochloric acid, hydrobromic acid, sulfuric acid, formic acid, trifluoroacetic acid, benzenesulfonic acid, p-toluenesulfonic acid, etc.)

Suitable reduction may include the ones as exemplified in Process 2.

Suitable Lewis acid may include aluminum trichloride and the like.

This elimination reaction is usually carried out in a conventional solvent such as water, methanol, ethanol, acetic acid or any other solvent which does not adversely influence the reaction.

This reaction temperature is not critical and the reaction is usually carried out at ambient temperature or under heating.

PROCESS 6

The compound $(I_a{}^7)$ or its salt can be prepared by subjecting the compound (V) or its salt to elimination reaction of the lower alkyl moiety at the lower alkoxy group.

Suitable salt of the compound (V) may include an inorganic or organic base salt as exemplified for the compound (Ia).

This reaction is preferably carried out in the presence of a hydrohalogenic acid (e.g. hydriodic acid, hydrobromic acid, etc.), a Lewis acid (e.g. aluminum trichloride, etc.) and the like.

This reaction is usually carried out in a solvent such as water, acetic anhydride, acetic acid or any other solvent which does not adversely influence the reaction.

This reaction temperature is not critical and the reaction is usually carried out at ambient temperature or under heating.

This invention includes, within its scope, the case that the protected carboxy is transformed into the free carboxy group during the reaction.

The processes for the preparation of the starting compounds (IIa), (IIb) and (IIc) of this invention are explained in details as follows.

PREPARATION A (a) Preparation of the compound (IX)

The compound (IX) can be prepared by reacting the compound (XI) or its salt with the compound (X).

The suitable salts of the compound (XI) may include an acid salt (e.g. hydrochloride, sulfate, etc.).

This reaction is usually carried out in the presence of a conventional solvent such as acetone, methanol, tetrahydrofuran, chloroform, benzene or any other solvent which does not adversely influence the reaction.

This reaction temperature is not critical and the reaction is usually carried out at ambient temperature or under heating.

Thus obtained compound (IX) can be used in the next step without isolation.

(b) Preparation of the compound (VIII)

The compound (VIII) can be prepared by subjecting the compound (IX) wherein $R^4$ is an acyl group, to deacylation reaction.

This deacylation reaction can be carried out in a conventional manner such as hydrolysis or the like. This hydrolysis can be carried out in the similar manner to that illustrated in Process 5.

(c) Preparation of the compound (VII)

The compound (VII) or its salt can be prepared by reacting the compound (VIII) with an oxidizing agent.

Suitable examples of the oxidizing agent may include halogen (e.g. chlorine, bromine, iodine, etc.), potassium ferricyanide and the like.

This reaction is usually carried out in a solvent such as dichloromethane, chloroform, benzene or any other solvent which does not adversely influence the reaction.

This reaction temperature is not critical and the reaction is usually carried out at ambient temperature or under heating.

(d) Preparation of the compound (VI)

The compound (VI) can be prepared by reacting the compound (VII) or its salt with a diazotizing agent and then reacting the resultant compound with a cupric halide.

Suitable salt of the compound (VII) may include the one as exemplified for the compound (XI).

Suitable examples of the diazotizing agent may include the ones as exemplified in Process 3.

The cupric halide may include cupric chloride, cupric bromide and the like.

This reaction is usually carried out in a solvent such as acetonitrile, benzene, chloroform or any other solvent which does not adversely influence the reaction.

This reaction temperature is not critical and the reaction is usually carried out under cooling or at ambient temperature.

(e) Preparation of the compound (IIa)

The compound (IIa) can be prepared by hydrolyzing the compound (VI).

This hydrolysis can be carried out in the similar manner to that illustrated in Process 5.

PREPARATION (B)

(a) Preparation of the compound (XII)

The compound (XII) or its salt can be prepared by reacting the compound (XIII) or its salt with a metal polysulfide.

Suitable salts of the compounds (XII) and (XIII) are the same as those exemplified for the compound (XI).

Suitable examples of the metal polysulfide may include alkali metal disulfide (e.g. sodium disulfide, potassium disulfide, etc.) and the like.

This reaction is usually carried out in a conventional solvent such as water, acetone, methanol, ethanol, aqueous methanol, aqueous acetone or any other solvent which does not adversely influence the reaction.

This reaction temperature is not critical and the reaction is usually carried out under heating.

(b) Preparation of the compound (IIa)

The compound (IIa) can be prepared by reacting the compound (XII) or its salt with a metal monosulfide and then reacting the resultant compound with phosgene.

In the first step, the compound (XII) or its salt is reacted with a metal monosulfide.

Suitable examples of the metal monosulfide may include alkali metal monosulfide (e.g. sodium monosulfide, potassium monosulfide, etc.) and the like.

This reaction is usually carried out in a conventional solvent such as water, methanol, ethanol, acetone, aqueous methanol, aqueous acetone or any other solvent which does not adversely influence the reaction.

This reaction temperature is not critical and the reaction is usually carried out at ambient temperature or under heating.

Thus obtained compound can be used in the next step without isolation.

In the second step, phosgene is reacted with the said produced compound to give the compound (IIa).

This reaction is usually carried out in a conventional solvent such as water, acetone, methanol, ethanol, toluene or any other solvent which does not adversely influence the reaction.

This reaction is preferably carried out in the presence of an inorganic or organic base as exemplified in Process 1.

This reaction temperature is not critical and the reaction is usually carried out at ambient temperature or under cooling.

PREPARATION C (a) Preparation of the compound (IIb)

The compound (IIb) can be prepared by reacting the compound (XIV) with a nitrating agent.

Suitable examples of the nitrating agent may include nitric acid, fuming nitric acid, a mixture of nitric acid and conc. sulfuric acid and the like.

This reaction can be carried out in the presence or absence of a solvent such as water or any other solvent which does not adversely influence the reaction.

This reaction temperature is not critical and the reaction is usually carried out under cooling or at ambient temperature.

(b) Preparation of the compound (IIc)

The compound (IIc) or its salt can be prepared by reducing the compound (IIb).

Suitable salts of the compound (IIc) are the same as those exemplified for the compound (XI).

This reduction can be carried out in substantially the same manner to that illustrated in Process 2.

The effective ingredient of the present pharmaceutical composition, i.e. the compound (I) or a pharmaceutical acceptable salt thereof is a highly potent inhibitor of aldose reductase. For illustrating this fact, some pharmacological data are shown in the following test.

TEST (INHIBITORY EFFECT ON RABBIT LENS ALDOSE REDUCTASE)

(I) Test Compound (1) 2-Oxo-5-chloro-6-phenoxy-3-benzothiazolineacetic acid.
(2) 2-Oxo-5-chloro-6-phenyl-3-benzothiazolineacetic acid
(3) 2-Oxo-6-phenoxy-3-benzothiazolineacetic acid
(4) 2-Oxo-6-(2-chlorophenoxy)-3-benzothiazolineacetic acid
(5) 2-Oxo-6-phenyl-7-chloro-3-benzothiazolineacetic acid
(6) 2-Oxo-5-chloro-6-cyclohexyl-3-benzothiazolineacetic acid
(7) 2-Oxo-5-chloro-6-phenyl-3-benzoxazolineacetic acid
(8) 2-Oxo-5-chloro-6-bromo-3-benzothiazolineacetic acid
(9) 2-Oxo-6-chloro-1-indolineacetic acid
(10) 2-Oxo-5-chloro-3-benzothiazolineacetic acid
(11) 2-Oxo-5-chloro-3-benzoxazolineacetic acid
(12) 2-Oxo-6-chloro-3-benzothiazolineacetic acid
(13) 2,3-dioxo-6-chloro-1-indolineacetic acid
(14) 2-Oxo-5-methyl-6-phenyl-3-benzothiazolineacetic acid
(15) 2-Oxo-5,6-dichloro-3-benzothiazolineacetic acid
(16) 2-Oxo-5-chloro-6-nitro-3-benzothiazolineacetic acid
(17) 2-Oxo-5-chloro-6-amino-3-benzothiazolineacetic acid (II) Test Method The inhibitory effect (%) of the prescribed test compound at various concentrations was determined in substantially the same manner as described in the Journal of Biological Chemistry Vol. 240, page 877 (1965), excepting that aldose reductase prepared from rabbit lens was used in place of that prepared from calf lens. 50% Inhibitory concentration ($IC_{50}$) of the test compound was graphically calculated from the inhibitory effect as determined above.

(III) Test Result

The test results are shown in the following table.

| Test Compound No. | IC$_{50}$ (M) |
|---|---|
| 1 | $5.0 \times 10^{-8}$ |
| 2 | $2.9 \times 10^{-8}$ |
| 3 | $6.9 \times 10^{-7}$ |
| 4 | $2.7 \times 10^{-7}$ |
| 5 | $1.2 \times 10^{-7}$ |
| 6 | $1.4 \times 10^{-7}$ |
| 7 | $4.9 \times 10^{-8}$ |
| 8 | $5.0 \times 10^{-8}$ |
| 9 | $2.7 \times 10^{-7}$ |
| 10 | $2.0 \times 10^{-7}$ |
| 11 | $2.5 \times 10^{-7}$ |
| 12 | $4.1 \times 10^{-7}$ |
| 13 | $3.0 \times 10^{-7}$ |
| 14 | $3.3 \times 10^{-8}$ |
| 15 | $3.8 \times 10^{-8}$ |
| 16 | $1.2 \times 10^{-7}$ |
| 17 | $1.0 \times 10^{-7}$ |

For the preventiveness and treatment of diabetic complications in mammals, the compound (I) or its pharmaceutically acceptable salt can be administered in admixture with pharmaceutically acceptable carriers, i.e. in the form of a pharmaceutical composition. The pharmaceutical composition of this invention can be formulated in the form of capsules, tablets, granules, powders, solutions, ophthalmic preparations (e.g. eyedrop, ointment), etc.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the object compounds is to be varied depending on various factors such as kind of diseases, weight and/or age of a patient, and further the kind of administration route. Preferable dosage of compound (I) or its pharmaceutically acceptable salt is usually selected from within a range of about 0.1–100 mg/kg/day, but not limited thereto.

The following preparations and examples are given for the purpose of illustrating this invention.

PREPARATION 1

(a) To a solution of ammonium thiocyanate (30.2 g) in anhydrous acetone (660 ml) was added dropwise benzoyl chloride (47.6 g) with stirring at 50° C. After refluxing for 1.5 hours, the mixture was cooled to ambient temperature. To the mixture containing benzoyl isothiocyanate was added dropwise a solution of 2-phenoxyaniline (47.6 g) in anhydrous acetone (300 ml). The reaction mixture was refluxed with stirring for 1.5 hours and then concentrated under reduced pressure to give crystals, which were washed twice with water and dried to give crystalline 1-(2-phenoxyphenyl)-3-benzoylthiourea.

(b) Thus produced 1-(2-phenoxyphenyl)-3-benzoylthiourea was dissolved in a mixture of 10% aqueous sodium hydroxide (660 ml) and methanol (530 ml) at 50° C. The reaction mixture was stirred for 30 minutes at 50° C. and then cooled with ice to give crystals, which were separated by filtration, washed with water and dried to give 1-(2-phenoxyphenyl)thiourea.

mp: 120°–124° C.

PREPARATION 2

The following compounds were prepared in substantially, the same manner as those of Preparation 1 (a) and (b), respectively.

(1)

(a) 1-(4-Phenoxyphenyl)-3-benzoylthiourea
mp: 123°–126° C.

(b) 1-(4-Phenoxyphenyl)thiourea
mp: 180°–184° C.

(2)

(a) 1-(3-Chloro-4-phenoxyphenyl)-3-benzoylthiourea
(b) 1-(3-Chloro-4-phenoxyphenyl)thiourea
mp: 116°–120° C.

(3)

(a) 1-[4-(2-Chlorophenoxy)phenyl]-3-benzoylthiourea
mp: 116°–119° C.

(b) 1-[4-(2-Chlorophenoxy)phenyl]thiourea
mp: 131°–132° C.

(4)

(a) 1-(2-Chloro-4-biphenlyl)-3-benzoylthiourea
mp: 123°–125° C.

(b) 1-(2-Chloro-4-biphenylyl)thiourea
mp: 155°–158° C.

PREPARATION 3

To a mixture of 1-(2-phenoxyphenyl)thiourea (53.4 g) in chloroform (100 ml) was added dropwise a solution of bromine (35.0 g) in chloroform (50 ml) with stirring under ice-cooling during 40 minutes. After refluxing for 1 hour and 40 minutes, the mixture was cooled to ambient temperature. To the resultant mixture was added water and then the mixture was alkalified with 5% sodium hydroxide aqueous solution. The chloroform layer was washed with water, dried over magnesium sulfate, concentrated under reduced pressure to give crystals, which were recrystallized twice from isopropyl alcohol to give 2-amino-4-phenoxybenzothiazole (25.8 g).

mp: 135°–137° C.

PREPARATION 4

The following compounds were prepared in substantially the same manner as that of Preparation 3.
(1) 2-Amino-6-phenoxybenzothiazole
  mp: 167°–169° C.
(2) 2-Amino-5-chloro-6-phenoxybenzothiazole
(3) 2-Amino-6-(2-chlorophenoxy)benzothiazole
  mp: 161°–167° C.

PREPARATION 5

(a) To a solution of 1-(2-chloro-4-biphenylylthiourea (5.3 g) in chloroform (150 ml) was added dropwise a solution of bromine (3.2 g) in chloroform (10 ml) with stirring at ambient temperature during 15 minutes. After the stirring was continued for 30 minutes at ambient temperature, the reaction mixture was refluxed for 5 hours and 15 minutes and then cooled to ambient temperature to give crystals, which were separated by filtration. To the crystals were added sodium bisulfite and aqueous sodium hydroxide. The mixture was extracted with ethyl acetate, washed with water, dried over magnesium sulfate and concentrated under reduced pressure to give a mixture of 2-amino-5-chloro-6-phenylbenzothiazole and 2-amino-6-phenyl-7-chlorobenzothiazole (4.1 g).

(b) To a mixture of anhydrous cupric bromide (4.2 g) in anhydrous acetonitrile (80 ml) was added dropwise t-butyl nitrite (2.6 g) with stirring under ice-cooling. To the mixture was added dropwise a mixture of 2-amino-5-chloro-6-phenylbenzothiazole and 2-amino-6-phenyl-7-chlorobenzothiazole (4.1 g) with stirring under ice-cooling during 10 minutes. After the stirring was continued under ice-cooling for 1 hour and 40 minutes, the reaction mixture was concentrated under reduced pressure to give a residue, to which was added dil. hydrochloric acid. The mixture was extracted with chloroform. The organic layer was separated, washed with water, dried over magnesium sulfate and concentrated under reduced pressure to give an oily residue, which was chromatographed on silica gel using a mixture of benzene and hexane (1:2) as eluants to give the first Fraction (A) and the second Fraction (B). The Fraction (A) gave crystalline 2-bromo-5-chloro-6-phenylbenzothiazole (1.0 g).
  mp: 105°–108° C.
  NMR: δppm (DMSO-d$_6$): 7.53 (5H, s), 8.25 (1H, s), 8.28 (1H, s).

Further, the Fraction (B) gave crystalline 2-bromo-6-phenyl-7-chlorobenzothiazole (1.5 g).
  mp: 105°–109° C.
  NMR δppm (DMSO-d$_6$): 7.57 (5H, s), 7.67 and 8.08 (2H, ABq, J=9 Hz).

PREPARATION 6

To a mixture of anhydrous cupric bromide (22.1 g) and anhydrous acetonitrile (320 ml) was added dropwise t-butyl nitrite (12.8 g) with stirring under ice-cooling. To the mixture was further added 2-amino-4-phenoxybenzothiazole (20.0 g) with stirring under ice-cooling during 25 minutes. After the stirring was continued for 1.5 hours under ice-cooling, acetonitrile was removed from the resultant mixture under reduced pressure to give a residue, which was dissolved in a small volume of dil. hydrochloric acid and extracted with ethyl acetate. The organic layer was washed with water, dried over magnesium sulfate, concentrated under reduced pressure to give oily residue, which was chromatographed on silica gel using a mixture of benzene and n-hexane (1:1) as eluants. The fractions containing the object compound were collected and crystallized to give 2-bromo-4-phenoxybenzothiazole (99 g).
  mp: 117°–121° C.

PREPARATION 7

The following compounds were prepared in substantially the same manner as that of Preparation 6.
(1) 2-Bromo-6-phenoxybenzothiazole oil;
  IR (film): 1605, 1590, 1560 cm$^{-1}$.
(2) 2-Bromo-5-chloro-6-phenoxybenzothiazole
  mp: 153°–154° C.
(3) 2-Bromo-6-(2-chlorophenoxy)benzothiazole oil;
  IR (film): 1600, 1580, 1560 cm$^{-1}$.

PREPARATION 8

To a sodium ethoxide solution prepared with sodium metal (460 mg) and anhydrous ethanol (50 ml) was added 2-bromo-4-phenoxybenzothiazole (3.0 g). The mixture was refluxed with stirring 45 minutes. The solvent was removed under reduced pressure to give a residue, to which was added 10% hydrochloric acid (30 ml) and acetone (50 ml). The resultant mixture was refluxed with stirring for 2 hours. The solvent was removed under reduced pressure to give a residue, which was recrystallized from a mixture of ethanol and n-hexane to give crystalline 2-oxo-4-phenoxybenzothiazoline (2.0 g).
  mp: 153°–155° C.

PREPARATION 9

The following compounds were prepared in substantially the same manner as that of Preparation 8.
(1) 2-Oxo-6-phenoxybenzothiazoline
  mp: 140°–145° C.
(2) 2-Oxo-5-chloro-6-phenoxybenzothiazoline
  mp: 237°–241° C.
(3) 2-Oxo-6-(2-chlorophenyl)benzothiazoline
  mp: 132°–133° C.
(4) 2-Oxo-5-chloro-6-phenylbenzothiazoline
  mp: 245°–249° C.
(5) 2-Oxo-6-phenyl-7-chlorobenzothiazoline
  mp: 256°–257° C.

PREPARATION 10

A mixture of sodium monosulfide nonahydrate (14.7 g) and sulfur (1.76 g) in water (50 ml) was stirred at 60° C. for an hour. The resultant sodium disulfide aqueous solution was added dropwise a solution of 3-nitro-4-chlorodiphenyl ether (24.9 g) in acetone (50 ml) with stirring at 60° C. during 30 minutes. The reaction mixture was refluxed with stirring for 45 minutes and then cooled to ambient temperature. Acetone was removed under reduced pressure to give crystals, which were separated by filtration and washed with a small volume of acetone to give yellowish crystalline bis(2-nitro-4-phenoxyphenyl) disulfide (13.2 g).
  mp: 118°–121° C.

PREPARATION 11

(a) To a solution of 1,4-dichlorobenzene (294 g) in anhydrous carbon disulfide (400 ml) was added anhydrous aluminum chloride (16.0 g). To the mixture was added dropwise chlorocyclohexane (96 g) with stirring at ambient temperature during 3 hours. After the stirring was continued for 3 hours at ambient temperature, the reaction mixture was allowed to stand overnight at ambient temperature. To the reaction mixture was added dil.hydrochloric acid with stirring. The organic layer was separated, washed with water, dried over magnesium sulfate, concentrated under reduced pressure and allowed to stand at ambient temperature for a while to give precipitates. The precipitates were removed by filtration. The filtrate was distilled under reduced pressure to give 1,4-dichloro-2-cyclohexylbenzene (47.0 g).

bp: 138° C./5 mm Hg.

(b) To a solution of 1,4-dichloro-2-cyclohexylbenzene (12.0 g) in conc. sulfuric acid (15 ml) was added dropwise a mixture of nitric acid (d=1.42, 4 ml) and conc.sulfuric acid (6 ml) with stirring under ice-cooling. After the stirring was continued for 10 minutes, ice-water was added to the reaction mixture to give an oily residue, which was extracted with ether, washed with water, dried over magnesium sulfate and concentrated under reduced pressure. The resultant oily residue was distilled under reduced pressure to give 1,4-dichloro-2-cyclohexyl-5-nitrobenzene (10.0 g).

bp: 170° C./2 mm Hg.

(c) Bis(2-nitro-4-chloro-5-cyclohexylphenyl) disulfide was prepared from 1,4-dichloro-2-cyclohexyl-5-nitrobenzene in substantially the same manner as that of Preparation 10.

mp: 183°-184° C.

PREPARATION 12

A mixture of bis(2-nitro-4-phenoxyphenyl) disulfide (13.2 g), sodium monosulfide.nonahydrate (36.7 g) in water was refluxed with stirring for 3 hours and then cooled to ambient temperature. To the resultant mixture was added 10% sodium hydroxide aqueous solution (50 ml). Phosgene was passed through the reaction mixture with stirring under ice-cooling until it was neutralized. The resultant mixture was acidified with hydrochloric acid, extracted with ethyl acetate, washed with water, dried over magnesium sulfate and concentrated under reduced pressure to give a residue, which was chromatographed on silica gel using benzene and a mixture of benzene and ethyl acetate (10:1) as eluants. The fractions containing object compound was concentrated under reduced pressure to give crystals, which were recrystallized from a mixture of benzene and n-hexane to give crystalline 2-oxo-5-phenoxybenzothiazoline (4.0 g).

mp: 145°-150° C.

PREPARATION 13

The following compound was prepared in substantially the same manner as that of Preparation 12.
(1) 2-Oxo-5-chloro-6-cyclohexylbenzothiazoline
 mp: 230°-231° C.

PREPARATION 14

To a mixture of 2-oxo-5-chlorobenzothiazoline (465 g) in conc.sulfuric acid (500 ml) was added dropwise a solution of nitric acid (d=1.42, 275 g) in conc.sulfuric acid (500 ml) with stirring at 10° C. during an hour. After the stirring was continued for an hour under ice-cooling, to the resultant mixture was added ice-water (10 liters) to give crystals, which were separated by filtration, washed with water and dried to give 2-oxo-5-chloro-6-nitrobenzothiazoline (539 g).

mp: 235° C. (dec.).

PREPARATION 15

The following compounds were prepared in substantially the same manner as that of Preparation 14.
(1) 2-Oxo-5-chloro-6-nitrobenzoxazoline
 mp: 196°-203° C.
(2) 2-Oxo-5-nitro-6-chloroindoline crystals;
 IR (Nujol): 1710, 1620, 1520, 1340, 1330 cm$^{-1}$.
 NMR (DMSO-d$_6$) δ(ppm): 3.55 (2H, s), 6.95 (1H, s), 7.93 (1H, s).
(3) 2-Oxo-5-methyl-6-nitrobenzothiazoline
 mp: >250° C.

PREPARATION 16

To a mixture of ethanol (200 ml) and water (40 ml) were added ammonium chloride (2.2 g) and iron metal (19.7 g). To the mixture was added 2-oxo-5-nitro-6-chloroindoline (12.5 g) at 60° C. After refluxing for 45 minutes, the reaction mixture was filtered under warm condition. The filter cake was washed with ethanol. The combined filtrate and washings were evaporated to dryness under reduced pressure to give 2-oxo-5-amino-6-chloroindoline (10.0 g).

EXAMPLE 1

A mixture of 2-oxo-4-phenoxybenzothiazoline (2.0 g), ethyl bromoacetate (1.7 g), potassium carbonate (1.4 g) in acetone (30 ml) was refluxed for an hour with stirring. After the resultant mixture was filtered, the filtrate was concentrated under reduced pressure to give a residue, which was recrystallized from a mixture of ethanol and n-hexane to give crystalline ethyl 2-oxo-4-phenoxy-3-benzothiazolineacetate (2.0 g).

mp: 96°-99° C.

EXAMPLE 2

The following compounds were prepared in substantially the same manner as that of Example 1.
(1) Ethyl 2-oxo-5-phenoxy-3-benzothiazolineacetate
 mp: 120°-122° C.
(2) Ethyl 2-oxo-6-phenoxy-3-benzothiazolineacetate
 mp: 79°-81° C.
(3) Ethyl 2-oxo-5-chloro-6-phenoxy-3-benzothiazolineacetate
 mp: 109°-111° C.
(4) Ethyl 2-oxo-6-(2-chlorophenoxy)-3-benzothiazolineacetate oil
(5) Ethyl 2-oxo-5-chloro-6-phenyl-3-benzothiazolineacetate
 mp: 130°-131° C.
(6) Ethyl 2-oxo-6-phenyl-7-chloro-3-benzothiazolineacetate
 mp: 147°-148° C.
(7) Methyl 2-oxo-5-chloro-6-cyclohexyl-3-benzothiazolineacetate
 mp: 133°-134° C.
(8) Ethyl 2-oxo-5-methoxy-3-benzothiazolineacetate
 mp: 83°-84° C.
(9) Ethyl 2-oxo-6-chloro-1-indolineacetate
 mp: 135°-136° C.
(10) Ethyl 2-oxo-5-chloro-6-nitro-3-benzothiazolineacetate
 mp: 170°-171° C.
(11) Ethyl 2-oxo-5-chloro-6-nitro-3-benzoxazolineacetate
 mp: 126.5°-128° C.
(12) Ethyl 2-(2-oxo-5-chloro-6-nitro-3-benzothiazoline)-propionate mp: 112°–114° C.
(13) Ethyl 2-oxo-5-methyl-6-nitro-3-benzothiazolineacetate
mp: 159°–160° C.

EXAMPLE 3

A mixture of ethyl 2-oxo-5-chloro-6-amino-3-benzothiazolineacetate (347.8 g) and conc.hydrochloric acid (1040 ml) was stirred for 30 minutes at ambient temperature. After the resultant mixture was cooled to 2° C., a solution of sodium nitrite (88.3 g) in water (120 ml) was added dropwise thereto below 5° C. in the course of 40 minutes. The mixture was stirred for 20 minutes at 0° C. To the resultant mixture was added benzene (5.2 l) in the course of 30 minutes. After the reaction mixture was stirred for an hour and 40 minutes under ice-cooling, a solution of sodium acetate.3H$_2$O (1.56 kg) in water (3.6 l) was added dropwise thereto under ice-cooling in the course of an hour. The mixture was stirred overnight at ambient temperature. The organic layer was separated, washed with water and dried over anhydrous magnesium sulfate, concentrated under reduced pressure to give a residue, which was recrystallized from ethanol to give ethyl 2-oxo-5-chloro-6-phenyl-3-benzothiazolineacetate (311.5 g).
mp: 130°–131° C.

EXAMPLE 4

The following compounds were prepared in substantially the same manner as that of Example 3.
(1) Ethyl 2-oxo-5-chloro-6-phenyl-3-benzoxazolineacetate.
mp: 99°–101° C.
(2) Ethyl 2-(2-oxo-5-chloro-6-phenyl-3-benzothiazoline)-propionate, oil.
IR (film): 1740, 1680 cm$^{-1}$.
(NMR (DMSO-d$_6$) δ(ppm): 1.13 (3H, t, J=7 Hz), 1.58 (3H, d, J=6 Hz), 4.13 (2H, q, J=7 Hz), 5.45 (1H, q, J=6 Hz), 7.2–7.7 (7H, m).
(3) Ethyl 2-oxo-5-phenyl-6-chloro-1-indolineacetate
mp: 132°–133° C.
(4) Ethyl 2-oxo-5-methyl-6-phenyl-3-benzothiazolineacetate.
mp: 138°–141° C.

EXAMPLE 5

To a solution of ethyl 2-oxo-5-chloro-6-phenoxy-3-benzothiazolineacetate (2.5 g) in methanol (100 ml) was added a solution of sodium hydroxide (360 mg) in water (10 ml). The reaction mixture was incubated for 15 minutes at 50° C. and then concentrated under reduced pressure to give a residue, which was acidified with dil.hydrochloric acid to give crystals, which were washed with water, dried and recrystallized from aqueous ethanol to give 2-oxo-5-chloro-6-phenoxy-3-benzothiazolineacetic acid (2.2 g).
mp: 190°–194° C.

EXAMPLE 6

To a solution of ethyl 2-oxo-5-chloro-6-phenyl-3-benzothiazolineacetate (269.6 g) in ethanol (5.4 l) was added dropwise a solution of sodium hydroxide (40.3 g) in water (540 ml) at 50° C. in the course of 5 minutes. After stirring for 15 minutes at 50° C., the mixture was cooled to ambient temperature to give crystals, which were separated by filtration and washed with ethanol and acetone to give crystalline sodium salt of 2-oxo-5-chloro-6-phenyl-3-benzothiazolineacetic acid (217.3 g).

The crystals were dissolved in water and acidified with dil.hydrochloric acid to give crude crystals, which were recrystallized from aqueous ethanol to give crystalline 2-oxo-5-chloro-6-phenyl-3-benzothiazolineacetic acid (131.9 g).
mp: 262°–266° C.

EXAMPLE 7

The following compounds were prepared in substantially the same manner as those of Examples 5 and 6.
(1) 2-Oxo-4-phenoxy-3-benzothiazolineacetic acid
mp: 148°–151° C.
(2) 2-Oxo-5-phenoxy-3-benzothiazolineacetic acid
mp: 179°–181° C.
(3) 2-Oxo-6-phenoxy-3-benzothiazolineacetic acid
mp: 150°–152° C.
(4) 2-Oxo-6-(2-chlorophenoxy)-3-benzothiazolineacetic acid
mp: 162°–164° C.
(5) 2-Oxo-6-phenyl-7-chloro-3-benzothiazolineacetic acid
mp: 254°–257° C.
(6) 2-Oxo-5-chloro-6-cyclohexyl-3-benzothiazolineacetic acid
mp: 222°–226° C.
(7) 2-(2-Oxo-5-chloro-6-phenyl-3-benzothiazoline)-propionic acid
mp: 202°–203° C.
(8) 2-Oxo-5-methyl-6-phenyl-3-benzothiazolineacetic acid
mp: 245°–250° C.
(9) 2-Oxo-5-methoxy-3-benzothiazolineacetic acid
mp: 171°–174° C.
(10) 2-Oxo-6-chloro-1-indolineacetic acid
mp: 215° C. (dec.)
(11) 2-Oxo-5-chloro-6-amino-3-benzothiazolineacetic acid
mp: 246°–249° C.

EXAMPLE 8

To a solution of ethyl 2-oxo-5-chloro-6-phenyl-3-benzoxazolineacetate (1.5 g) in acetic acid (10 ml) was added conc.hydrochloric acid (5 ml). The reaction mixture was stirred at 60° C. for 1.5 hours and then cooled to ambient temperature. The resultant mixture was diluted with water to precipitate crystals, which were separated by filtration, washed with water, dried and then recrystallized from a mixture of chloroform and acetone to give 2-oxo-5-chloro-6-phenyl-3-benzoxazolineacetic acid.
mp: 200°–203° C.

EXAMPLE 9

The following compounds were prepared in substantially the same manner as that of Example 8.
(1) 2-Oxo-5-phenyl-6-chloro-1-indolineacetic acid
mp: 260°–262° C.
(2) 2-Oxo-5-chloro-6-nitro-3-benzothiazolineacetic acid
mp: 240°–243° C. (dec.)

EXAMPLE 10

To a mixture of 57% hydriodic acid (50 ml) and acetic anhydride (15 ml) was added a solution of ethyl 2-oxo-5-methoxy-3-benzothiazolineacetate (2.67 g) in acetic acid (15 ml). The reaction mixture was refluxed with stirring for 1.5 hours and then cooled to ambient temperature. To the resultant mixture were added ice-water and a small volume of sodium bisulfite. The mixture was extracted with ethyl acetate. The extract was washed with water, dried over magnesium sulfate and concentrated under reduced pressure to give crystalline 2-oxo-5-hydroxy-3-benzothiazolineacetic acid (1.7 g).

mp: 217°–221° C.

EXAMPLE 11

(a) To a solution of methyl 2-oxo-5-chloro-3-benzothiazolineacetate (10 g) in dioxane (100 ml) was added dropwise bromine (2 ml) with stirring at 25°–30° C. during 40 minutes. After the stirring was continued at ambient temperature for 4 hours, precipitates in the resultant mixture were separated by filtration, washed with dioxane and diethylether and dried to give crystalline methyl 2-oxo-5-chloro-6-bromo-3-benzothiazolineacetate (8.38 g).

mp: 209°–210° C.

(b) A mixture of methyl 2-oxo-5-chloro-6-bromo-3-benzothiazolineacetate (2.0 g), methanol (250 ml) and 10% sodium hydroxide aqueous solution (2.5 ml) was refluxed with stirring for 1.5 hours and then cooled with ice-water to give crystals, which were separated by filtration. The filtrate was concentrated under reduced pressure to give crystals. The combined crystals were dissolved in water (80 ml) under heating and then insoluble materials were removed by filtration. The filtrate was adjusted at pH 2–3 with 10% hydrochloric acid and cooled to give crystals, which were separated by filtration, washed with water and dried to give crystalline 2-oxo-5-chloro-6-bromo-3-benzothiazolineacetic acid (1.5 g).

mp: 249°–252° C.

EXAMPLE 12

The following compounds were prepared in substantially the same manner as those of Example 11 (a) and (b), respectively.

(a) Ethyl 2-oxo-5,6-dichloro-3-benzothiazolineacetate
mp: 147°–149° C.
(b) 2-Oxo-5,6-dichloro-3-benzothiazolineacetic acid
mp: 256°–258° C.

EXAMPLE 13

To a mixture of ethanol (10 liters) and water (1 liter) were added ammonium chloride (25 g) and iron metal (300 g). To the mixture was added ethyl 2-oxo-5-chloro-6-nitro-3-benzothiazolineacetate (434.6 g) under mild reflux. After refluxing with stirring for 4 hours, the resultant mixture was filtered under warm condition. The filter cake was washed with ethanol. The combined filtrate and washings were concentrated under reduced pressure and cooled to ambient temperature to give crystals, which were separated by filtration to give crystalline ethyl 2-oxo-5-chloro-6-amino-3-benzothiazolineacetate (347.8 g).

mp: 154°–160° C.

EXAMPLE 14

The following compounds were prepared in substantially the same manner as that of Example 13.
(1) Ethyl 2-oxo-5-chloro-6-amino-3-benzoxazolineacetate.
mp: 137°–141° C.
(2) Ethyl 2-(2-oxo-5-chloro-6-amino-3-benzothiazoline)propionate.
mp: 105°–106° C.
(3) Ethyl 2-oxo-5-methyl-6-amino-3-benzothiazolineacetate.

mp: 140°–142° C.

EXAMPLE 15

To a mixture of 2-oxo-5-amino-6-chloroindoline (3.2 g), potassium carbonate (4.8 g) and acetone (60 ml) was added dropwise ethyl chloroacetate (3.2 g) at ambient temperature. The reaction mixture was refluxed with stirring for 4 hours and then filtered under warm condition. The filter cake was washed with acetone. The combined filtrate and washings were concentrated under reduced pressure to give a residue, which was purified by a column chromatography on silica gel to give crystalline ethyl 2-oxo-5-amino-6-chloro-1-indolineacetate (0.9 g).

IR (Nujol): 3440, 3330, 3220, 1750, 1690, 1590 cm$^{-1}$.

NMR δppm (CDCl$_3$): 6.64 (1H, s), 6.55 (1H, s), 4.34 (2H, s), 4.19 (2H, q, J=7 Hz), 3.44 (2H, s), 1.27 (3H, t, J=7 Hz).

EXAMPLE 16

| | |
|---|---|
| 2-Oxo-5-chloro-6-phenyl-3-benzothiazoline-acetic acid | 500 (g) |
| Starch | 1987 |
| Magnesium stearate | 13 |

The above ingredients are blended and filled in hard gelatin-capsules, in a conventional manner, to give 10,000 capsules, each of which contains 50 mg of an active ingredient, 2-oxo-5-chloro-6-phenyl-3-benzothiazolineacetic acid.

EXAMPLE 17

| | |
|---|---|
| 2-Oxo-5-chloro-3-benzothiazolineacetic acid | 250 (g) |
| Starch | 1980 |
| Magnesium stearate | 20 |

The above ingredients are blended and filled in hard gelatin-capsules, in a conventional manner, to give 10,000 capsules, each of which contains 25 mg of an active ingredient, 2-oxo-5-chloro-3-benzothiazolineacetic acid.

EXAMPLE 18

| | |
|---|---|
| 2-Oxo-5-chloro-3-benzoxazolineacetic acid | 20000 (g) |
| Lactose | 10400 |
| Starch | 3600 |
| Ethyl cellulose | 1800 |
| Magnesium stearate | 200 |

The above ingredients are blended and compressed, in a conventional manner, into 10,000 tablets weighing 360 mg, each of which contains 200 mg of an active ingredient, 2-oxo-5-chloro-3-benzoxazolineacetic acid. Thus obtained tablets are, when desired, coated with sugar-coating, film-coating or enteric-coating.

We claim:
1. A compound of the formula:

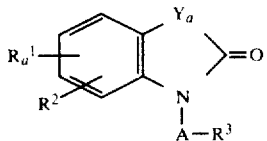

wherein
R$_a^1$ is halogen, nitro, amino, (C$_3$ to C$_8$)cycloalkyl, phenyl or phenoxy
R$^2$ is halogen or C$_1$-C$_6$ alkyl,
R$^3$ is carboxy or esterified lower alkoxycarbonyl,
Y$_a$ is sulfur, and
A is C$_1$-C$_6$ alkylene,
and pharmaceutically acceptable salts thereof.

2. A compound of claim 1, wherein
R$_a^1$ is halogen, phenyl or phenoxy,
R$^2$ is halogen or C$_1$-C$_6$ alkyl,
R$^3$ is carboxy.

3. A compound of claim 2, which is selected from the groups consisting of
2-oxo-5,6-dichloro-3-benzothiazolineacetic acid,
2-oxo-5-chloro-6-bromo-3-benzothiazolineacetic acid,
2-oxo-5-chloro-6-phenyl-3-benzothiazolineacetic acid,
2-oxo-5-methyl-6-phenyl-3-benzothiazolineacetic acid,
2-oxo-5-chloro-6-phenoxy-3-benzothiazolineacetic acid,
and pharmaceutically acceptable salt thereof.

4. An aldose reductase inhibiting pharmaceutical composition which comprises, as an effective ingredient, at least one compound of the formula:

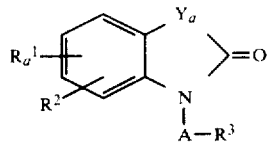

wherein
R$_a^1$ is halogen, nitro, amino, (C$_3$ to C$_8$)cycloalkyl, phenyl or phenoxy
R$^2$ is halogen or C$_1$-C$_6$ alkyl,
R$^3$ is carboxy or lower alkoxycarbonyl,
Y$_a$ is sulfur, and
A is C$_1$-C$_6$ alkylene,
or pharmaceutically acceptable salts thereof with a pharmaceutically acceptable carrier.

* * * * *